United States Patent
Taghizadeh et al.

(10) Patent No.: US 9,993,748 B2
(45) Date of Patent: Jun. 12, 2018

(54) CENTRIFUGE CLIP AND METHOD

(71) Applicant: AuxoCell Laboratories, Inc., Cambridge, MA (US)

(72) Inventors: Rouzbeh R. Taghizadeh, Cambridge, MA (US); Paul Puniello, Providence, RI (US)

(73) Assignee: Auxocell Laboratories, Inc., Cambridge, MA (US)

( * ) Notice: Subject to any disclaimer, the term of this patent is extended or adjusted under 35 U.S.C. 154(b) by 269 days.

(21) Appl. No.: 14/822,982

(22) Filed: Aug. 11, 2015

(65) Prior Publication Data

US 2016/0038946 A1    Feb. 11, 2016

Related U.S. Application Data

(60) Provisional application No. 62/035,616, filed on Aug. 11, 2014.

(51) Int. Cl.
  *B01D 21/26* (2006.01)
  *B04B 5/04* (2006.01)
  (Continued)

(52) U.S. Cl.
  CPC ......... *B01D 21/262* (2013.01); *A61M 1/0209* (2013.01); *A61M 1/029* (2013.01); *B04B 5/0428* (2013.01); *A61M 1/3693* (2013.01)

(58) Field of Classification Search
  CPC ... B01D 21/262; A61M 1/0209; A61M 1/029; A61M 1/3693; A61M 1/3695;
  (Continued)

(56) References Cited

U.S. PATENT DOCUMENTS 1,389,604 A    9/1921   Silverman
3,171,184 A    3/1965   Lage
(Continued)

FOREIGN PATENT DOCUMENTS

EP    1228806 A1    8/2002
EP    1385609 A1    2/2004
(Continued)

OTHER PUBLICATIONS

International Search Report and Written Opinion for PCT/US2012/064130, dated Jan. 25, 2013, 16 pages.
(Continued)

*Primary Examiner* — Timothy C Cleveland
(74) *Attorney, Agent, or Firm* — Calfee, Halter & Griswold LLP

(57) ABSTRACT

A clip of the present application generally comprises a first clip member, a second clip member, and a retention feature. The first clip member and the second clip member are coupled together and capable of being placed in at least two positions. In the first position, the clip is capable of receiving a bag containing a fluid, and, in the second position, the bag is capable of being held between the first and second clip members. While the clip is holding the bag, two or more pockets are formed in the bag, and the fluid is generally restricted or prohibited from transferring from one pocket to another pocket while the clip is in this position. A retention feature retains the clip, which is holding a bag, to a centrifuge receptacle and allows the clip to be placed in a predetermined position on the centrifuge receptacle.

6 Claims, 9 Drawing Sheets

(51) Int. Cl.
*A61M 1/02* (2006.01)
*A61M 1/36* (2006.01)

(58) Field of Classification Search
CPC ....... B04B 5/0428; B04B 5/0435; B04B 7/08; B04B 7/12
See application file for complete search history.

(56) References Cited

U.S. PATENT DOCUMENTS

| | | | |
|---|---|---|---|
| 3,257,726 A | 6/1966 | Longobardi | |
| 3,380,499 A | 4/1968 | Vocci et al. | |
| 3,545,671 A * | 12/1970 | Ross | A61B 5/15003 383/38 |
| 3,666,187 A | 5/1972 | Norris | |
| 4,151,959 A | 5/1979 | Deister | |
| 4,307,846 A | 12/1981 | Spelberg | |
| 4,487,205 A | 12/1984 | Di Giovanni et al. | |
| 4,509,695 A | 4/1985 | Bessman | |
| D284,810 S | 7/1986 | Kelemen, Sr. | |
| D299,008 S | 12/1988 | N/a/ slund | |
| 4,828,395 A | 5/1989 | Saito et al. | |
| 4,887,335 A | 12/1989 | Folkmar | |
| 5,428,871 A | 7/1995 | Iosif | |
| 5,604,959 A | 2/1997 | Bowen | |
| D384,459 S | 9/1997 | Eisenman | |
| D390,447 S | 2/1998 | Colen, Jr. | |
| 5,713,108 A | 2/1998 | Solomon et al. | |
| 5,731,199 A | 3/1998 | Roggero et al. | |
| D423,353 S | 4/2000 | Blanchard et al. | |
| 6,120,474 A | 9/2000 | Okuda et al. | |
| 6,138,425 A | 10/2000 | Wendt | |
| 6,786,739 B2 | 9/2004 | Frutschy et al. | |
| 6,817,750 B1 | 11/2004 | Sands | |
| 6,863,431 B2 | 3/2005 | Yacko et al. | |
| 6,863,675 B2 | 3/2005 | Wilson, Jr. | |
| 6,890,728 B2 | 5/2005 | Dolecek et al. | |
| 7,052,172 B2 | 5/2006 | Jahn et al. | |
| 7,060,494 B2 | 6/2006 | Bhat | |
| 7,062,822 B2 | 6/2006 | Folkmar | |
| 7,172,334 B2 | 2/2007 | Chiappetta | |
| 7,270,284 B2 | 9/2007 | Liao et al. | |
| 7,306,741 B2 | 12/2007 | Dolecek et al. | |
| 7,326,223 B2 | 2/2008 | Wilson, Jr. | |
| 7,611,473 B2 | 11/2009 | Boock et al. | |
| D605,361 S | 12/2009 | Hsu | |
| D625,174 S | 10/2010 | Karekar et al. | |
| 7,897,388 B2 | 3/2011 | Shetty et al. | |
| 8,034,003 B2 | 10/2011 | Pesce et al. | |
| 8,048,952 B2 | 11/2011 | Wynne et al. | |
| 8,119,121 B2 | 2/2012 | Fraser et al. | |
| 8,278,102 B2 | 10/2012 | Ennis et al. | |
| 8,367,409 B2 | 2/2013 | Abbot et al. | |
| D716,601 S | 11/2014 | Taghizadeh et al. | |
| D717,587 S | 11/2014 | Taghizadeh et al. | |
| 8,893,995 B2 | 11/2014 | Taghizadeh et al. | |
| 2002/0197631 A1 | 12/2002 | Lawrence et al. | |
| 2003/0054331 A1 | 3/2003 | Fraser et al. | |
| 2003/0161818 A1 | 8/2003 | Weiss et al. | |
| 2004/0193071 A1 | 9/2004 | Binette et al. | |
| 2004/0197367 A1 | 10/2004 | Rezania et al. | |
| 2005/0139704 A1 | 6/2005 | Liao et al. | |
| 2005/0148071 A1 | 7/2005 | Davies et al. | |
| 2006/0192038 A1 | 8/2006 | Sekine | |
| 2007/0082389 A1 | 4/2007 | Clark et al. | |
| 2007/0259330 A1 | 11/2007 | Goddard et al. | |
| 2008/0069895 A1 | 3/2008 | Liu et al. | |
| 2008/0118477 A1 | 5/2008 | Christopherson | |
| 2008/0132803 A1 | 6/2008 | Friedlander | |
| 2008/0152630 A1 | 6/2008 | Ginis et al. | |
| 2008/0196602 A1 | 8/2008 | Sands | |
| 2008/0274087 A1 | 11/2008 | Li et al. | |
| 2008/0305148 A1 | 12/2008 | Fu | |
| 2009/0022696 A1 | 1/2009 | Bernstein et al. | |
| 2009/0068153 A1 | 3/2009 | Vitelli et al. | |
| 2009/0074731 A1 | 3/2009 | Librach et al. | |
| 2009/0081171 A1 | 3/2009 | Fu et al. | |
| 2009/0124007 A1 | 5/2009 | Cho | |
| 2009/0136988 A1 | 5/2009 | Reschiglian et al. | |
| 2009/0142835 A1 | 6/2009 | Kobayashi et al. | |
| 2009/0170059 A1 | 7/2009 | Klingemann | |
| 2009/0232781 A1 | 9/2009 | Fu | |
| 2009/0232782 A1 | 9/2009 | Fu | |
| 2009/0280093 A1 | 11/2009 | Friedlander | |
| 2009/0291061 A1 | 11/2009 | Riordan et al. | |
| 2010/0034783 A1 | 2/2010 | Son et al. | |
| 2010/0098675 A1 | 4/2010 | Tankovich | |
| 2010/0104539 A1 | 4/2010 | Daniel et al. | |
| 2010/0247495 A1 | 9/2010 | Ichim et al. | |
| 2010/0326460 A1 | 12/2010 | Hsu | |
| 2011/0002883 A1 | 1/2011 | Petrikovsky et al. | |
| 2011/0112559 A1 | 5/2011 | Monassevitch et al. | |
| 2011/0151556 A1 | 6/2011 | Kallis et al. | |
| 2011/0158969 A1 | 6/2011 | Chopp | |
| 2011/0189254 A1 | 8/2011 | Liu et al. | |
| 2011/0256186 A1 | 10/2011 | Font Perez et al. | |
| 2011/0274664 A1 | 11/2011 | Harn et al. | |
| 2011/0293667 A1 | 12/2011 | Baksh et al. | |
| 2011/0312091 A1 | 12/2011 | Zhao et al. | |
| 2012/0073090 A1 | 3/2012 | Szellos | |
| 2012/0083803 A1 | 4/2012 | Patel et al. | |
| 2012/0093783 A1 | 4/2012 | Pinkernell et al. | |
| 2012/0095484 A1 | 4/2012 | Dominguez | |
| 2012/0141595 A1 | 6/2012 | Tseng et al. | |
| 2012/0171762 A1 | 7/2012 | Coelho et al. | |
| 2012/0189583 A1 | 7/2012 | Liu et al. | |
| 2012/0214659 A1 | 8/2012 | Do et al. | |
| 2012/0258459 A1 | 10/2012 | Huang | |
| 2012/0270314 A1 | 10/2012 | Ding et al. | |
| 2012/0276215 A1 | 11/2012 | Riordan et al. | |
| 2012/0276518 A1 | 11/2012 | Gillis | |
| 2012/0294909 A1 | 11/2012 | Daniel et al. | |
| 2012/0315259 A1 | 12/2012 | Friedlander | |
| 2013/0034524 A1 | 2/2013 | Agha-Mohammadi | |
| 2013/0059286 A1 | 3/2013 | Chang et al. | |
| 2013/0059383 A1 | 3/2013 | Dijkhuizen Borgart et al. | |
| 2013/0121972 A1 | 5/2013 | Taghizadeh | |
| 2013/0183273 A1 | 7/2013 | Taghizadeh | |
| 2013/0295673 A1 | 11/2013 | Taghizadeh | |

FOREIGN PATENT DOCUMENTS

| | | |
|---|---|---|
| GB | 1152418 A | 5/1969 |
| JP | S6143981 | 3/1986 |
| JP | S6143982 | 3/1986 |
| WO | 2003086598 A1 | 10/2003 |
| WO | 2005030936 | 4/2005 |

OTHER PUBLICATIONS

Castaneda, "Laboratory Diagnosis of Brucellosis in Man" Bull. Org. Mond. Bull. Wld. Hth Org. Sante, 1961, 24, pp. 73-84.
Fossum et al., "Minced Skin for Tissue Engineering of Epithelialized Subcutaeous Tunnels" Tissue Eng Part A., Aug. 2009; 15(8):pp. 2085-2092.
D'Allessandris et al., "Autoclavable Dispensing Device" Air Force Aerospace Medical Research Laboratory, Feb. 1980, 8 pages.
Amazon Customer Reviews Ikea Sealing Clip, review date Dec. 10, 2013, online, http://www.amazon.com/Ikea-Sealing-402-312-87 Assorted-Colors/dp/9178900549/ref=cm_cr_pr_product_top?ie=UTF8, [site visited Jun. 24, 2015 5:05:52 PM].
Cardinal Health:BMP Cytology Funnel clip, google website publish date Sep. 2, 2008, online, http://extww02a.cardinal.com/us/en/distributedproducts/ASP/B4200-597A.asp?cat=laboratory, [site visited Jun. 24, 2015] 8:37:27 PM].
Dialysis Tubing Closure Carolina.com, customer review date Jan. 27, 2010, online, http://www.carolina.com/dialysis-ubing/dialysis-tubing-closure/684239.pr,[site visited Jun. 24, 2015 9:48:41 PM].

\* cited by examiner

CENTRIFUGE CLIP AND METHOD

CROSS-REFERENCE TO RELATED APPLICATION

This application claims the benefit of and priority to U.S. Provisional Patent Application Ser. No. 62/035,616, entitled "CENTRIFUGE CLIP AND METHOD" and filed Aug. 11, 2014, the entire disclosure of which is incorporated herein by reference.

BACKGROUND

Collecting a concentrated cellular pellet is generally performed by placing solid tubes containing a solution of cells diluted with saline through centrifugation. After centrifugation of the tubes, a decantation process is performed to separate the cells from the supernatant. The purpose of this process is to obtain desired cells from the original solution. However, using solid tubes creates a problem because the process of placing the cells in the solid tubes makes the process an open system, as opposed to a closed system, which potentially affects the sterility of the process.

SUMMARY

A closed system containing components used to collect cells without exposing the cells to things that may compromise their sterility is desirable. Exemplary closed systems transport the cells into a bag without allowing the cells to be exposed to anything outside of the system. The bag is then put through a centrifugation process. The clip, system, and methods of the present application are used with these systems to facilitate collection of a concentrated cellular pellet using the centrifugation process without compromising the sterility of the cells. However, it should be understood that the clip, system, and methods of the present application may be used with other systems, including non-sterile systems. Further, the devices and methods of the present application may be used with the centrifugation of mixtures containing other materials, such as, for example, blood or other bodily fluids, mixtures used in food processing and manufacturing, or mixtures used in chemical processing and manufacturing.

Further, without the use of the clip described herein, the use of the bag during centrifugation may not be desirable because scattered cell packing may occur, which potentially leads to a loss of cells during decanting of the supernatant. For example, the clip of the present application is configured to suspend the bag during centrifugation, allowing the bag to hang and stretch and prohibiting the formation of creases or folds in the bag. Creases or folds in the bag cause scattered cell packing because the cells will settle at various locations within the bag (e.g., on the creases or folds) and not necessarily in a concentrated cellular pellet. Thus, it is desirable to minimize any creasing or folding of the bag during the centrifugation process. As such, when the clip of the present application is used, there is not a significant loss of cells during decanting of the supernatant.

The present application discloses a clip for use with a bag during centrifugation, a system for collecting a sediment using centrifugation, and a method for collecting a sediment using centrifugation.

In certain embodiments, the clip of the present application comprises a first clip member, a second clip member, and a retention feature. The first clip member and the second clip member are coupled together and capable of being placed in two positions. In the first position, the clip is capable of receiving a bag containing a fluid, and, in the second position, the bag is capable of being held between the first and second clip members. While the clip is holding the bag, two or more pockets are formed in the bag, and the fluid is generally restricted or prohibited from transferring from one pocket to another pocket while the clip is in this position.

In certain embodiments, the retention feature retains the clip, which is holding a bag, to a centrifuge receptacle. As used herein, the centrifugation receptacle may be the centrifuge bucket or a receptacle adapter used with the bucket. When the clip is used with a centrifuge receptacle, the clip is generally a sufficient length to fit across the centrifuge receptacle, but not so long as to prohibit the centrifuge receptacle from swinging freely. The retention feature allows the clip to be placed in a predetermined position on the centrifuge receptacle. In certain embodiments, the system of collecting a sediment comprises flexible bags and the clip of the present application.

In certain embodiments, the method of collecting a sediment comprises attaching the clip of the present application to a flexible bag that is holding a mixture. The clip is placed on a centrifuge receptacle in a predetermined position that allows the flexible bag to be suspended within the centrifuge receptacle. A centrifugation process is performed on the centrifuge receptacle in which the flexible bag is suspended. The clip and bag are removed from the centrifuge receptacle. The clip is released from the bag by moving the clip from a second position to a first position. The supernatant is moved from the pocket of the bag that is containing the sediment to a separate pocket.

DETAILED DESCRIPTION

As stated above, it is desirable for the process of collecting cells to remain sterile. For example, U.S. Patent Publication No. 2013/0295673 describes a system that can be used to collect cells and maintain sterility of the cells. The entire contents of U.S. Patent Publication No. 2013/0295673, filed on Jul. 1, 2013 and titled "Systems and Methods for Processing Cells," is hereby incorporated by reference. As shown and described in this application, a closed system is used to place extracted cells into a bag, which maintains the sterility of the cells. The system comprises multiple components. For example, a tissue mincing tool is used to extract the cells. The extracted cells are then placed in a bag without compromising the sterility of the cells. After the extracted cells are placed in the bag, a centrifugation process is performed to collect a concentrated cellular pellet.

In order to place the bag through a centrifugation process, the bag may be placed in a conventional centrifugation receptacle. However, placing the bag within the centrifuge receptacle without any way to support the bag will allow creases to form in the bag. If creases are formed in the bag, cell packing will occur at various locations within the bag. This scattered cell packing leads to a potential loss of cells during the decanting of the supernatant. The present application discloses a device for holding and suspending the bag containing the extracted cells during centrifugation. The device is used to suspend the centrifuge bag from a rotating portion of the centrifuge during centrifugation such that no creases are formed in the bag.

The clip of the present application is configured to hold the bag of extracted cells and attach to the centrifuge receptacle, or other rotary portion of the centrifuge, so that the bag is suspended and not creased. For example, in certain embodiments, the clip is attached to the rim of a receptacle and the bag is suspended in the receptacle. The clip generally separates the bag into two or more pockets. During centrifugation, the clip prohibits a solution containing the cells from transferring from one pocket into another pocket. Packing occurs in the pocket containing the cellular solution. After centrifugation, during the decantation process, the packed cells remain in the pocket in which the solution was originally located and the supernatant is transported into another pocket.

Figure 1:
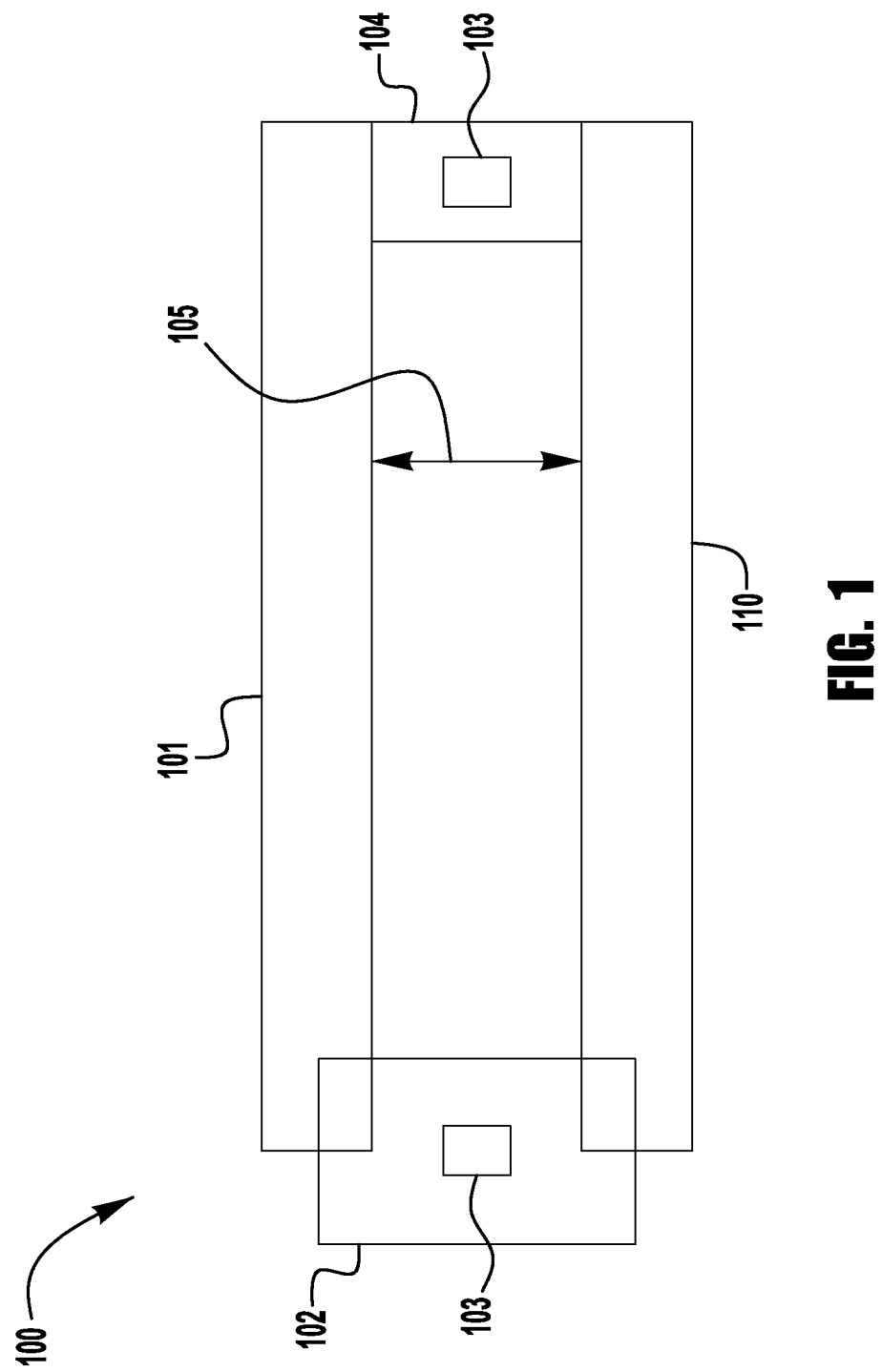
FIG. 1 schematically illustrates a clip according to an embodiment of the present application.

FIG. 1 schematically illustrates a clip 100 that is capable of holding and suspending a bag during centrifugation according to an embodiment of the present application. The clip 100 comprises a first clip member 101, a second clip member 110, and one or more retention features 103. When used with a centrifuge receptacle, the clip 100 is generally long enough to fit across a centrifuge receptacle 801 (see, e.g., FIGS. 8 and 9). However, if the clip 100 is too long, the clip 100 may prohibit the centrifuge receptacle from swinging freely. In certain embodiments, the length of the clip 100 is between about 80 mm and about 130 mm. In one embodiment, the length of the clip 100 is about 110 mm.

As illustrated in FIG. 1, the first clip member 101 and the second clip member 110 are coupled together at connection 104 and are movable between a first and second position. In the first position, the clip 100 forms a space or opening 105 between the clip members 101, 110 capable of receiving a bag (see, e.g., FIG. 7) containing a solution of cells. In the second position, the clip members 101, 110 are moved together such that the bag containing the solution is held between the clip members. While the clip 100 is holding the bag in the second position, the space 105 between the clip members 101, 110 is such that pockets are formed in the bag and fluid is restricted or prohibited from transferring from one pocket to the other pocket.

It should be understood that the first and second clip members 101 and 110 may be coupled in a wide variety of ways. For example, in certain embodiments, one end of the clip members are pivotally coupled together such that pivotal movement of the first clip member relative to the second clip member moves the clip between the first and second positions. In other embodiments, both ends of the clip members are coupled together such that movement of the first clip member towards and away from the second clip member moves the clip between the first and second positions. In still other embodiments, the first and second clip members are separate components and are coupled together (e.g., snapped together) only when the clip is in the second position.

The retention feature 103 retains the clip 100, which is holding a bag, to a part of the centrifuge, such as a rotating part of the centrifuge. For example, in certain embodiments, the retention feature 103 allows the clip 100 to be placed in a predetermined position on a centrifuge receptacle (see, e.g., FIG. 8). However, the retention feature 103 may be used to suspend the bag from other parts of the centrifuge during centrifugation such that no creases are formed in the bag.

Figure 2:
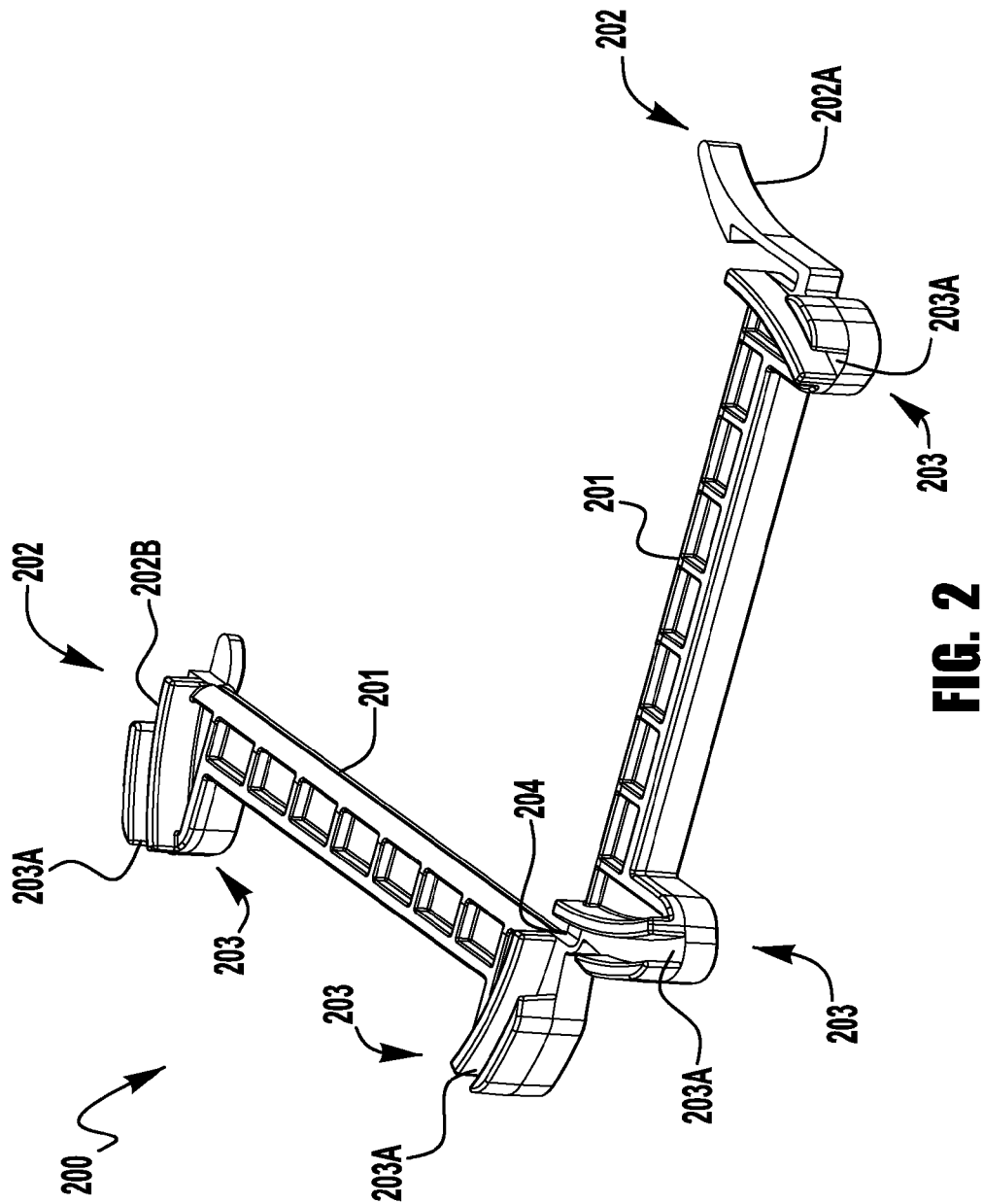
FIG. 2 is a bottom perspective view of a clip in an open position according to an embodiment of the present application.
Figure 3:
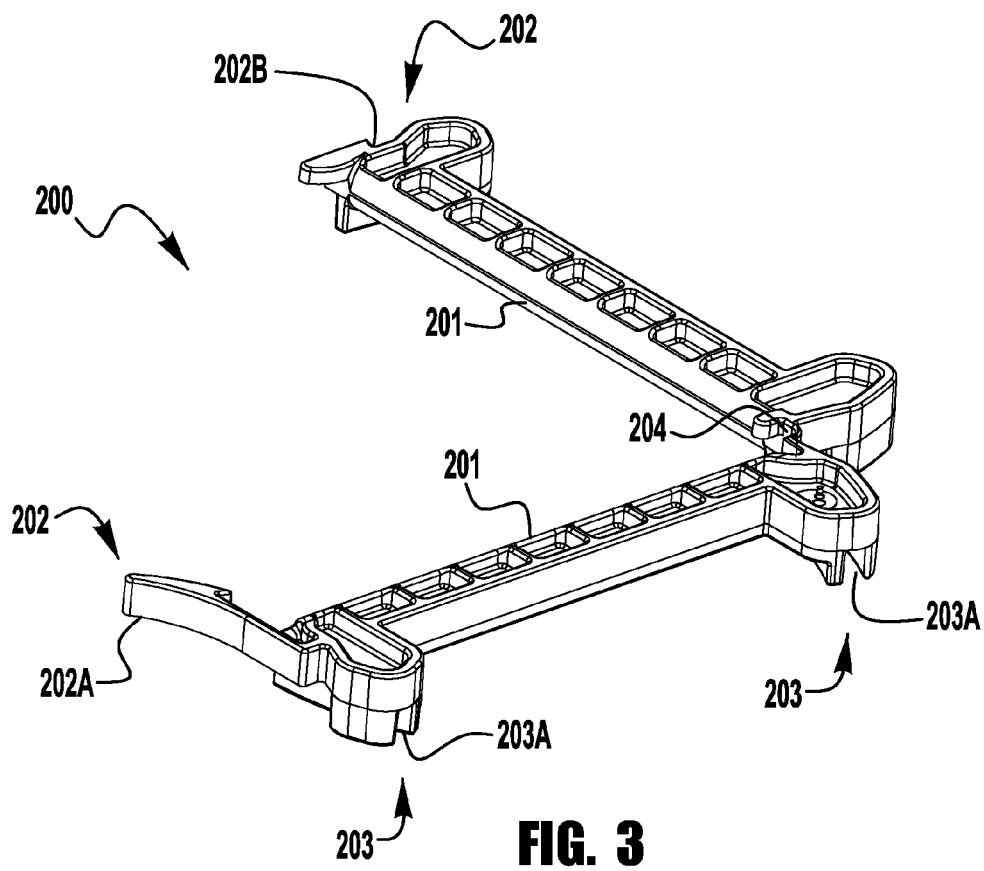
FIG. 3 is a top perspective view of the clip of FIG. 2 in the open position according to an embodiment of the present application.
Figure 4:
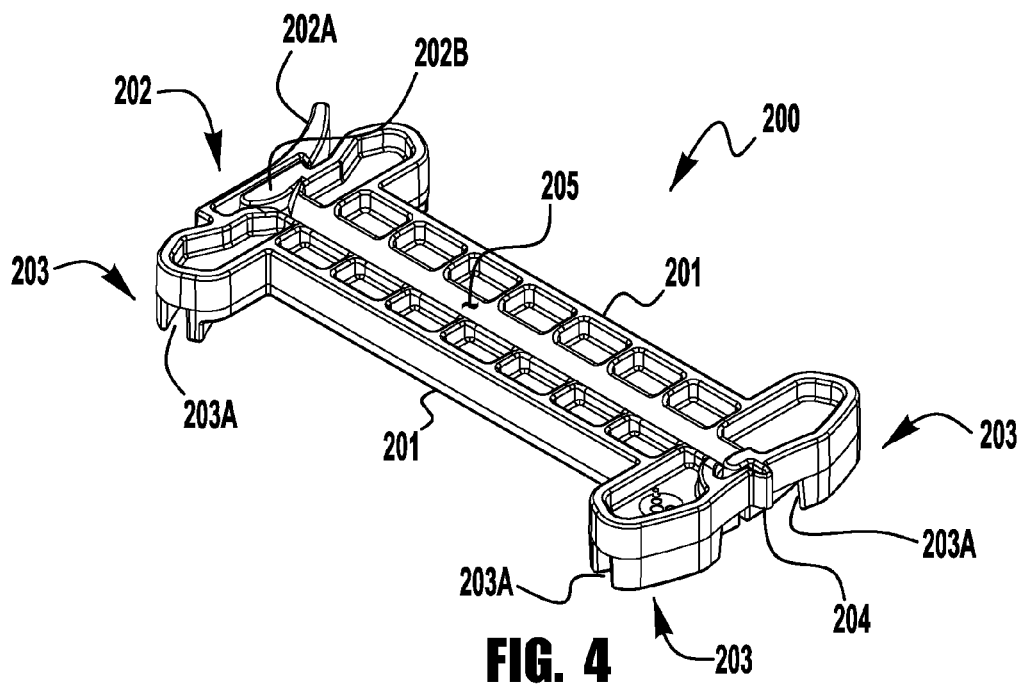
FIG. 4 is a top perspective view of the clip of FIG. 2 in a closed position according to an embodiment of the present application.
Figure 5:
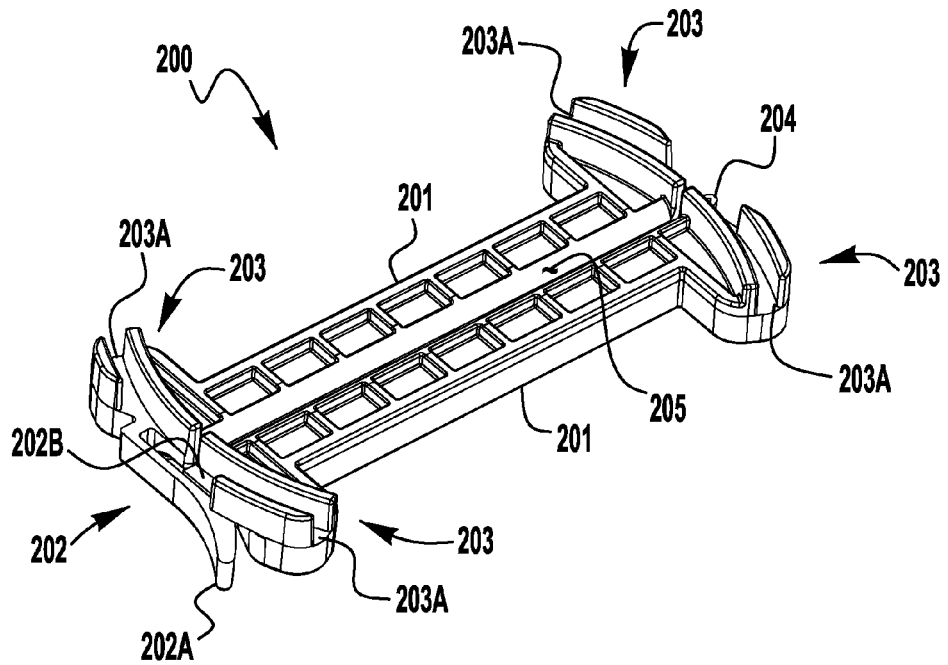
FIG. 5 is a bottom perspective view of the clip of FIG. 2 in the closed position according to an embodiment of the present application.

The retention feature 103 of the clip 100 may take a wide variety of forms capable of suspending the bag during centrifugation. For example, in certain embodiments, the retention feature holds the clip 100 and bag to a centrifuge receptacle during centrifugation. The retention feature 103 may comprise one or more grooves 203 (FIG. 2) designed to fit over the lip of a centrifuge receptacle. The retention feature 103 may also comprise one or more shoulders designed to fit over the lip of a centrifuge receptacle. In another embodiment, an adhesive may be used to hold the clip 100 on the centrifuge receptacle or other rotary portions of the centrifuge. In another embodiment, a spring-loaded pin or clip may be used to hold the centrifuge clip 100 on the centrifuge receptacle or other rotary portions of the centrifuge. However, a variety of other ways to hold the centrifuge clip 100 on the centrifuge may be used, such as with threads, friction fit, snap fit, etc.

A locking mechanism 102 is generally used to hold the clip 100 in the second position. The locking mechanism 102 may take a wide variety of forms. For example, the locking mechanism 102 may comprise a first locking member that engages a second locking member to hold the clip members 101 together when the clip 100 is in the second position. For example, the locking members may comprise a detent, latch, tongue and groove, hasp, or other locking device. In another embodiment, the locking mechanism 102 may comprise a locking member that engages one or more clip members 101 to hold the clip members 101 together when the clip 100 is in the second position. For example, the locking mechanism 102 may comprise a fastener, elastic band, wire, or the like. In another embodiment, the locking mechanism 102 may comprise an adhesive that is used to hold the clip 100 in the second position.

FIGS. 2-6 illustrate another embodiment of a clip 200 of the present application. As shown, the clip 200 comprises two clip members 201 that are pivotally coupled together at a connection 204 and movable between a first and second position. While the clip 200 is in the second position, a space 205 is formed between the clip members 201 that restricts or prohibits the movement of fluid between the clip members 201. A locking mechanism 202 holds the clip members 201 together in the second position. The locking mechanism 202 comprises two locking members (202A, 202B)—an extended member 202A that engages an indented member 202B.

As shown in FIGS. 2-6, a retention feature 203 allows the clip to be retained on the lip of a centrifuge receptacle. The retention feature 203 comprises grooves or channels 203A on each end of the clip members 201 that are sized and shaped to fit over the lip of a conventional centrifuge receptacle. The diameter of the opening of a conventional centrifuge receptacle may be between about 90 mm and about 110 mm, about 90 mm, or about 97 mm.

Figure 6:
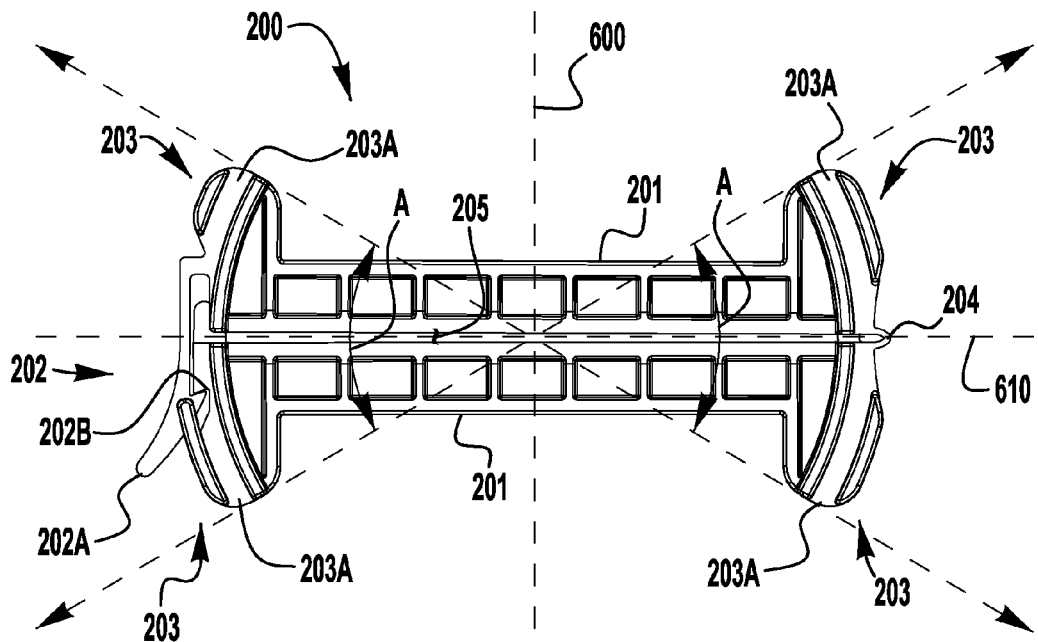
FIG. 6 is a bottom view of the clip of FIG. 2 in the closed position according to an embodiment of the present application.

The channels 203A of the retention feature 203 are curved to extend about the circumference of the lip of a centrifuge receptacle. As shown in FIG. 6, each curved channel 203A extends at an angle A. The angle A is generally between about 45 degrees and about 75 degrees. This range for angle A allows the clip to be stable and not lopsided when holding the bag while allowing sufficient space for the folded bag. In one embodiment, the angle A is about 60 degrees. In certain embodiments, however, the retention feature comprises one or more channels that extend substantially about the entire circumference of the lip of a centrifuge receptacle. Also, in certain embodiments, the retention feature (e.g., one or more channels) may comprise threads to couple the clip to the centrifuge receptacle.

As shown in FIGS. 7-10, while the clip 100 is in the second position and holding a bag 701, two or more pockets 703 are formed in the bag 701. The clip 200 restricts or prohibits the solution containing the cells 702 from transferring between pockets 703 during centrifugation. The space 205 between the first clip member 201 and second clip member 201, while the clip is in the second position, should be such that a solution containing cells 702 is restricted or prohibited from moving into a different pocket 703. Thus, the clip 200 holds the bag 701 and prohibits the flow of fluid between pockets 703. The bag of the present application may be a closeable or re-sealable bag which may be open at one or more end.

Figure 10:
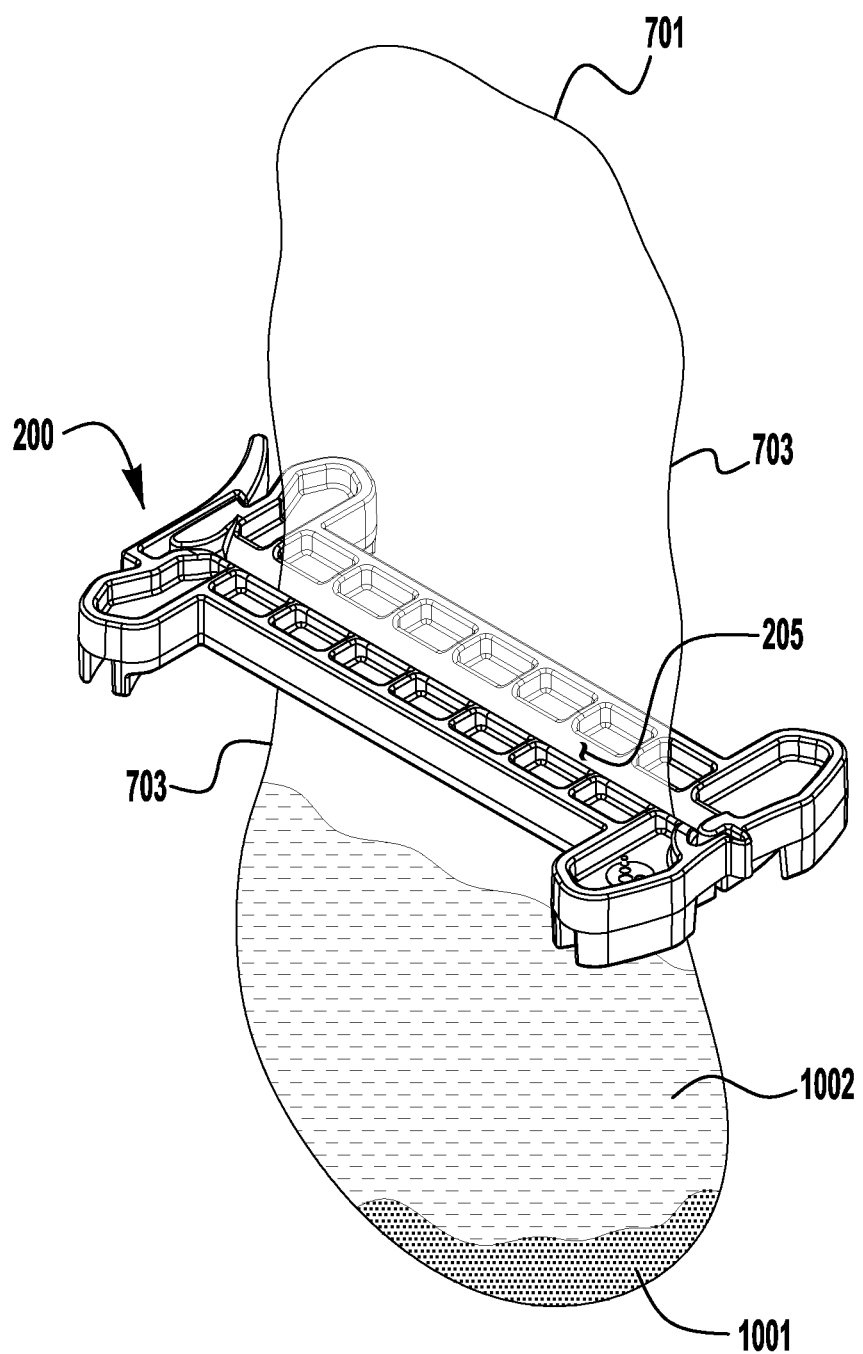
FIG. 10 is a perspective view of the clip of FIG. 2 removed from the centrifuge receptacle and holding the bag containing packed cells and supernatant after centrifugation.
Figure 11:
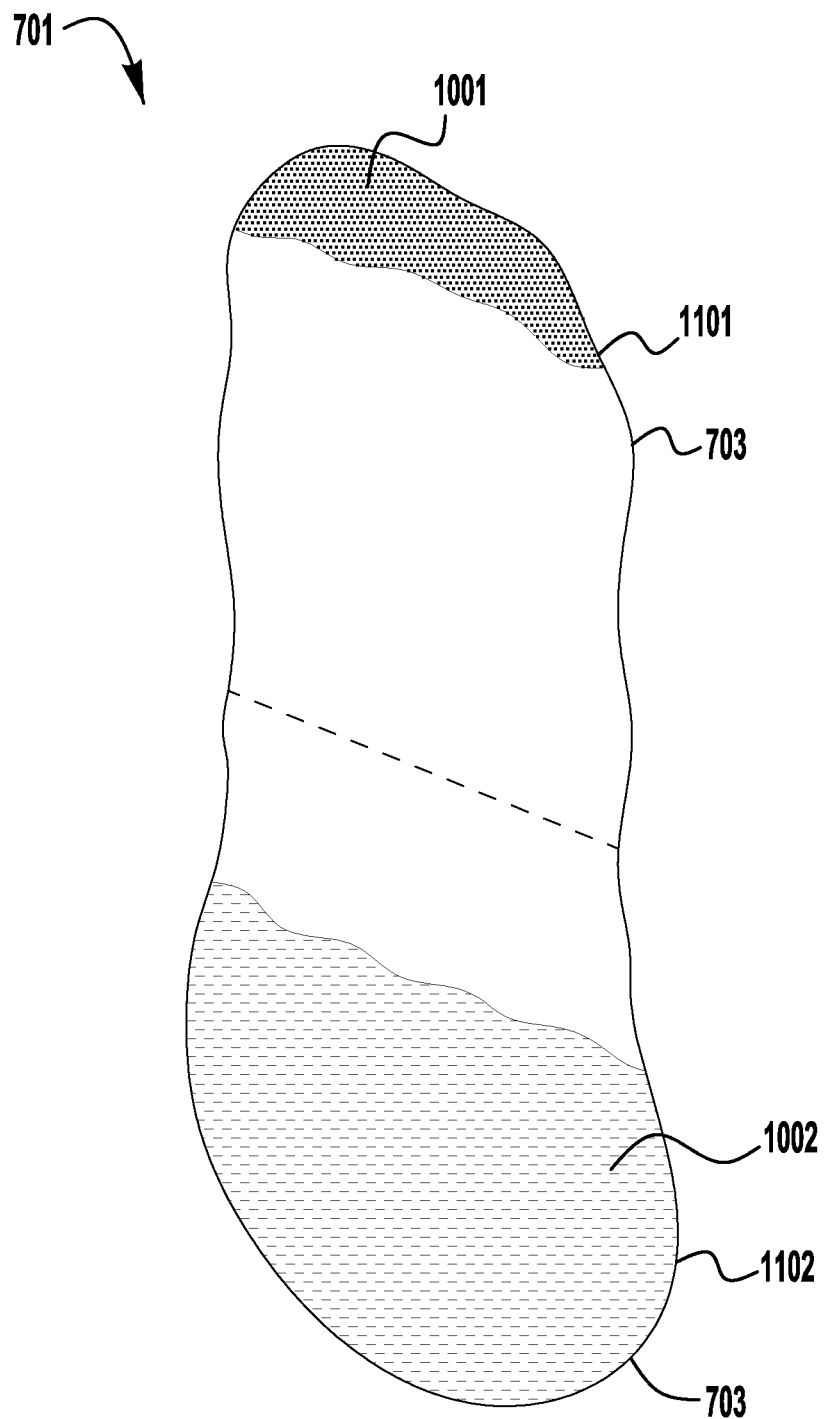
FIG. 11 schematically illustrates a bag containing packed cells and supernatant after the cells and supernatant have been separated into separate pockets of the bag.

FIG. 10 illustrates the clip 200 holding the bag 701 after centrifugation, wherein the solution containing cells was divided into two parts—the desired cells 1001 and the supernatant 1002. As shown in FIG. 11, after the clip 200 was moved from the second position back to the first position, the supernatant 1002 will be able to be transferred into a different pocket 703 in the bag 701, thus leaving the desired cells 1001 alone in the original pocket 1101 in which the solution containing the cells 702 was placed. In certain embodiments, the supernatant 1002 may also be desired after centrifugation in lieu of, or in addition to, the cells 1001.

Figure 7:
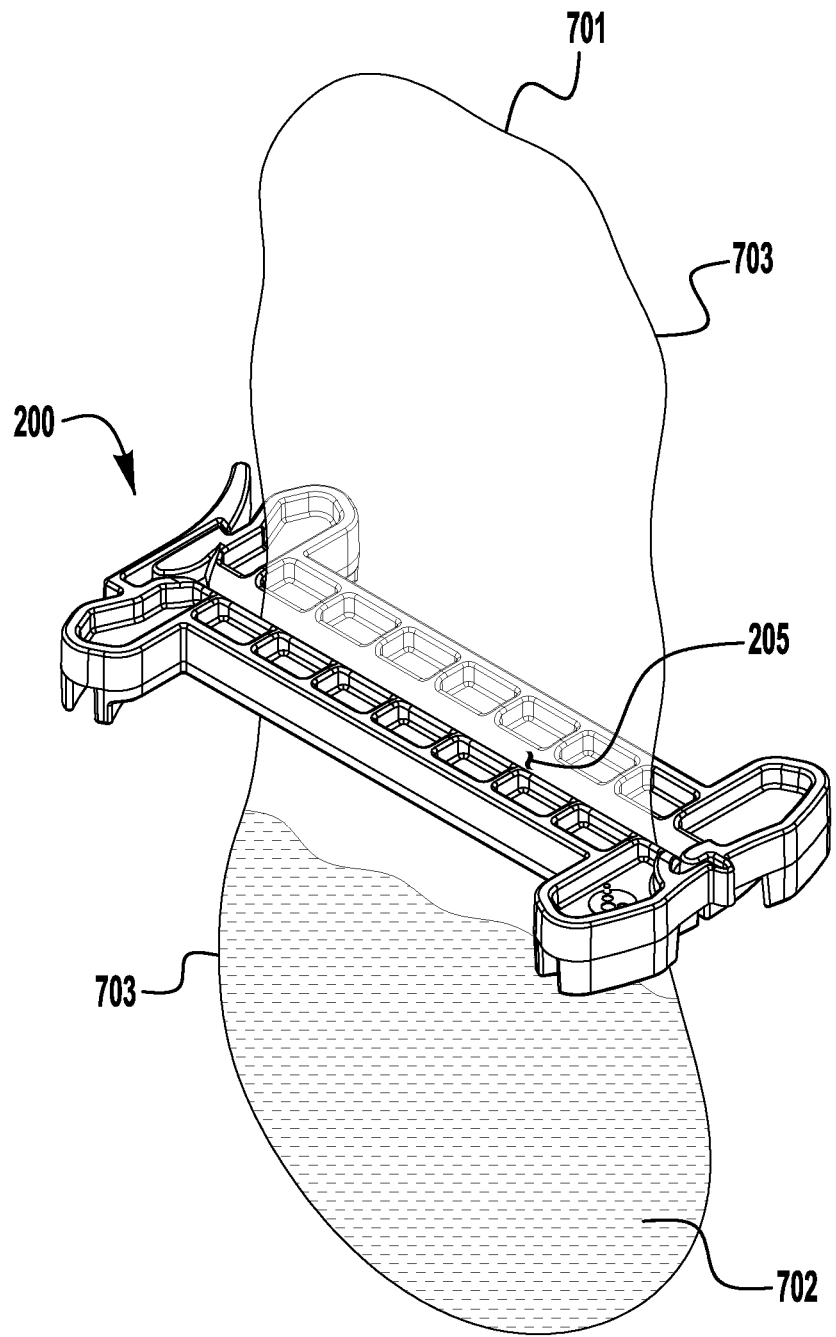
FIG. 7 is a top perspective view of the clip of FIG. 2 in the closed position and holding a transparent bag containing a solution that includes cells according to an embodiment of the present application.

An exemplary method for collecting a concentrated cellular pellet involves attaching the clip 200 of the present application to a flexible bag 701 that is holding a solution containing cells 702. FIG. 7 provides an illustration of the clip 200 of the present application attached to a bag 701 containing a solution containing cells 702.

Figure 8:
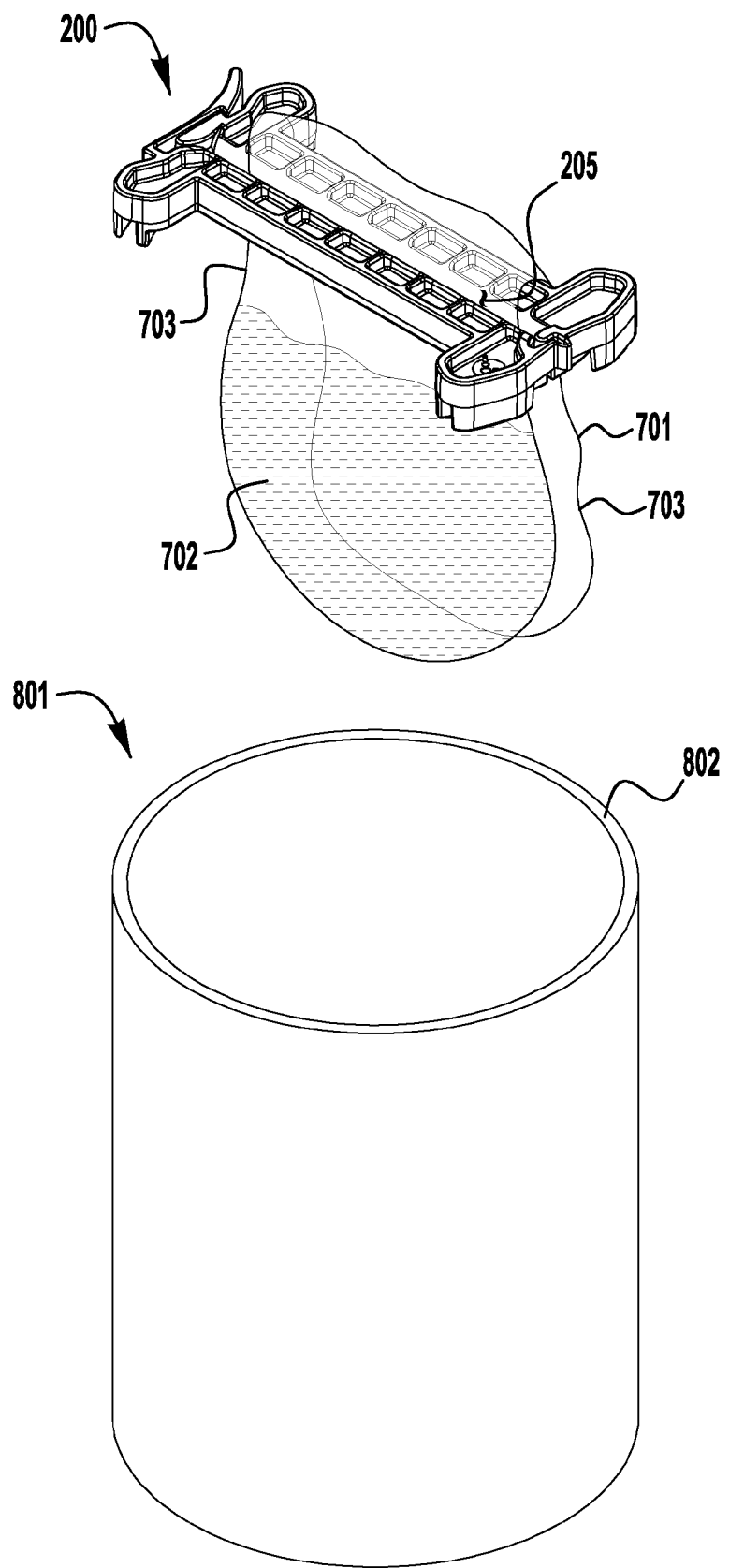
FIG. 8 is a top perspective view of the clip of FIG. 2 in the closed position and holding the bag after the bag is folded over the clip according to an embodiment of the present application, wherein the bag is shown being inserted into a centrifuge receptacle.
Figure 9:
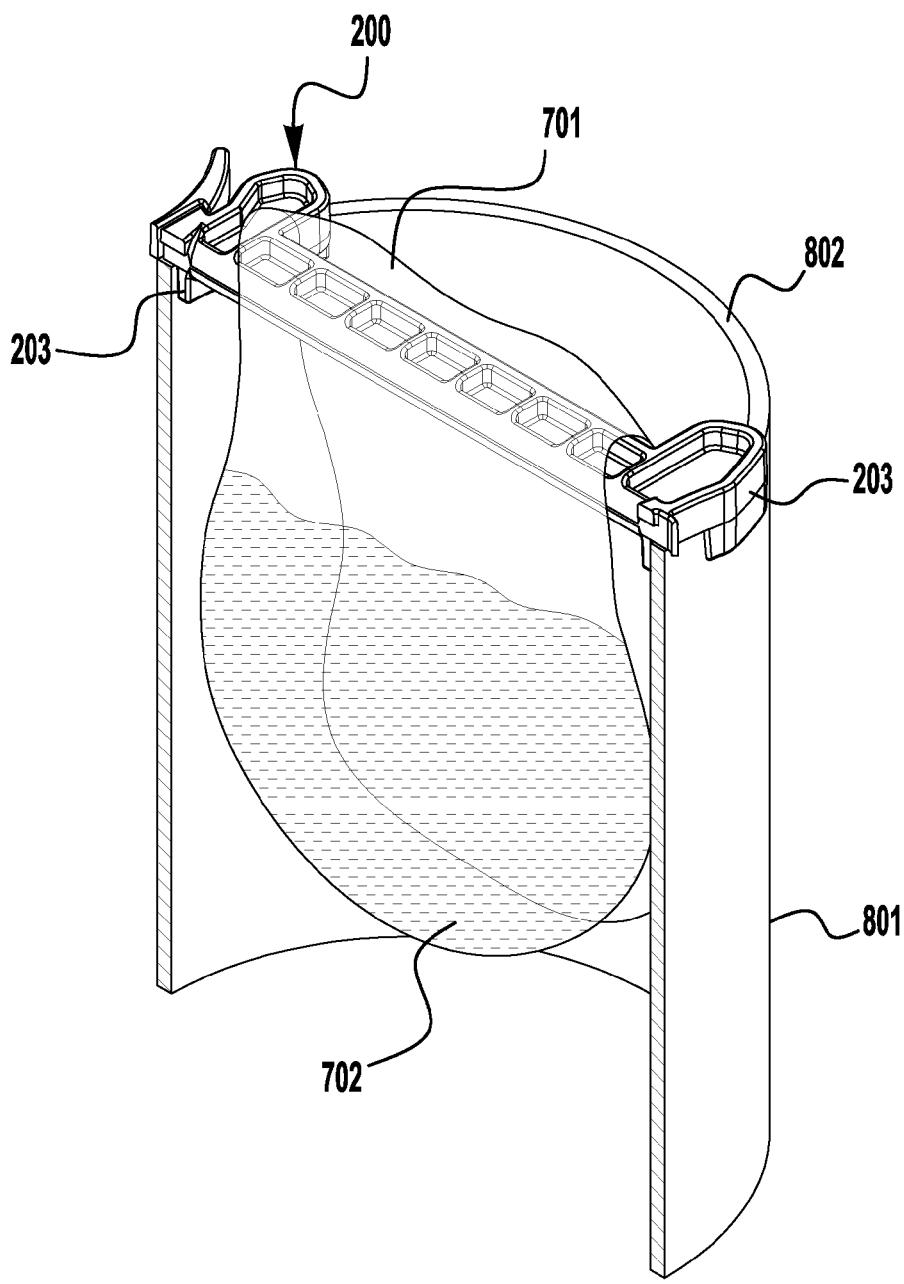
FIG. 9 is a cross-sectional perspective view of the clip of FIG. 2 retained in a predetermined position on the centrifuge receptacle and suspending the bag containing the solution within the centrifuge receptacle.

As shown in FIGS. 8-9, the clip 200 holding the flexible bag 701 is placed into the centrifuge receptacle 801. The clip 200 is placed in a predetermined position such that the flexible bag 701 is suspended within the centrifuge receptacle 801. In one application, the flexible bag 701 can be suspended within the centrifuge receptacle 801 by folding the bag 701 over the clip 200. A centrifuge generally has headroom constraints in the area above a centrifuge receptacle 801, and folding the bag 701 over the clip 200 allows the bag 701 to fit within the centrifuge receptacle 801 and not interfere with the headroom constraints of the centrifuge.

The centrifugation process is then performed. During the centrifugation process, the solution containing the cells 702 will separate into two parts—the desired cells and the supernatant. During this separation, cell packing will occur with the desired cells.

As shown in FIG. 10, after the centrifugation process, the clip 200 and bag 701 are removed from the centrifuge receptacle 801. At this point, the desired cells 1001 and the supernatant 1002 are in the same pocket 1101 of the bag 701.

As shown in FIG. 11, after the clip 200 is moved from the second position to the first position, the supernatant 1002 is then transferred from the pocket 1101 in the bag 701 containing the desired cells 1001 to a separate pocket 1102 by, for example, rotating the bag 701 to move the supernatant 1002 from one pocket 1101 to another pocket 1102. Thus, the desired cells 1001 will be packed together in one pocket 1101, and the supernatant 1002 will be in a separate pocket 1102. FIG. 11 shows the bag 701, after it has been rotated, wherein the desired cells 1001 are in one pocket 1101, which is the pocket 703 that the solution containing cells was originally located, and the supernatant 1002 is in a separate pocket 1102. Further, a bag press or separation stand may be used to extract the cells 1001 from the bag 701. For example, a bag press or separation stand having a biased or spring loaded face that compresses the bag 701 to hold the cells 1001 while the supernatant 1002 is removed may be used.

As described herein, when one or more components are described as being connected, joined, affixed, coupled, attached, or otherwise interconnected, such interconnection may be direct as between the components or may be in direct such as through the use of one or more intermediary components. Also as described herein, reference to a "member," "component," or "portion" shall not be limited to a single structural member, component, or element but can include an assembly of components, members or elements.

While the present invention has been illustrated by the description of embodiments thereof, and while the embodiments have been described in considerable detail, it is not the intention of the applicants to restrict or in any way limit the scope of the invention to such details. Additional advantages and modifications will readily appear to those skilled in the art. For example, where components are releasably or removably connected or attached together, any type of releasable connection may be suitable including for example, locking connections, fastened connections, tongue and groove connections, etc. Still further, component geometries, shapes, and dimensions can be modified without changing the overall role or function of the components. Therefore, the inventive concept, in its broader aspects, is not limited to the specific details, the representative apparatus, and illustrative examples shown and described. Accordingly, departures may be made from such details without departing from the spirit or scope of the applicant's general inventive concept.

While various inventive aspects, concepts and features of the inventions may be described and illustrated herein as embodied in combination in the exemplary embodiments, these various aspects, concepts and features may be used in many alternative embodiments, either individually or in various combinations and sub-combinations thereof. Unless expressly excluded herein all such combinations and sub-combinations are intended to be within the scope of the present inventions. Still further, while various alternative embodiments as to the various aspects, concepts and features of the inventions—such as alternative materials, structures, configurations, methods, devices and components, alternatives as to form, fit and function, and so on—may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the present inventions even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure, however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention, the inventions instead being set forth in the appended claims. Descriptions of exemplary methods or processes are not limited to inclusion of all steps as being required in all cases, nor is the order that the steps are presented to be construed as required or necessary unless expressly so stated.

What is claimed is:

1. A method for collecting a sediment using centrifugation comprising:

attaching a clip to a flexible bag that is holding a mixture, wherein the clip comprises a first clip member and a second clip member coupled to the first clip member, and wherein, when in a first position, the first and second clip members form a space capable of receiving the bag and, when in a second position, the bag is held between the first and second clip members creating two or more pockets in the bag, and a retention feature that retains the clip and bag to a centrifuge receptacle during centrifugation;

placing the clip on the centrifuge receptacle to keep the clip in a predetermined position wherein the clip is placed so that the flexible bag is suspended within the centrifuge receptacle; and performing a centrifugation process on the centrifuge receptacle in which the clip and flexible bag is located;

removing the clip from the centrifuge receptacle;

releasing the clip from the bag by moving the clip from the second position to the first position; and transferring a supernatant from the bag, wherein the supernatant is separated from the sediment.

2. The method of claim 1 wherein the retention feature of the clip comprises one or more grooves that are used to place the clip on the centrifuge receptacle.

3. The method of claim 1 wherein the retention feature of the clip comprises one or more shoulders that are used to place the clip on the centrifuge receptacle.

4. The method of claim 1 wherein the retention feature comprises an adhesive used to place the clip on the centrifuge receptacle.

5. The method of claim 1 wherein the retention feature of the clip comprises a spring-loaded pin that is used to place the clip on the centrifuge receptacle.

6. The method of claim 1 wherein the length of the first and second clip members is between about 80 mm and about 130 mm.

* * * * *